(12) United States Patent
Suzuki

(10) Patent No.: US 9,657,139 B2
(45) Date of Patent: May 23, 2017

(54) LIQUID RESOL-TYPE PHENOLIC RESIN

(71) Applicant: SUMITOMO BAKELITE CO., LTD., Tokyo (JP)

(72) Inventor: Yuji Suzuki, Fujieda (JP)

(73) Assignee: SUMITOMO BAKELITE CO., LTD., Tokyo (JP)

( * ) Notice: Subject to any disclaimer, the term of this patent is extended or adjusted under 35 U.S.C. 154(b) by 0 days.

(21) Appl. No.: 14/625,337

(22) Filed: Feb. 18, 2015

(65) Prior Publication Data

US 2015/0158979 A1  Jun. 11, 2015

Related U.S. Application Data

(63) Continuation of application No. 13/979,063, filed as application No. PCT/JP2011/080405 on Dec. 28, 2011, now abandoned.

(30) Foreign Application Priority Data

Jan. 14, 2011 (JP) .................................. 2011-005440

(51) Int. Cl.
| | | |
|---|---|---|
| *C07C 39/21* | (2006.01) | |
| *C08G 73/02* | (2006.01) | |
| *C08G 8/08* | (2006.01) | |
| *C08G 8/10* | (2006.01) | |

(52) U.S. Cl.
CPC ............ *C08G 73/024* (2013.01); *C07C 39/21* (2013.01); *C08G 8/08* (2013.01); *C08G 8/10* (2013.01)

(58) Field of Classification Search
CPC ........ C07C 39/21; C08G 73/024; C08G 8/08; C08G 8/10
See application file for complete search history.

(56) References Cited

U.S. PATENT DOCUMENTS

| | | | |
|---|---|---|---|
| 4,215,161 A * | 7/1980 | Seibold | .............. B29C 70/04 264/29.5 |
| 4,656,239 A | 4/1987 | Waitkus et al. | |
| 6,569,918 B2 | 5/2003 | Waitkus et al. | |
| 2006/0252855 A1 | 11/2006 | Pisanova et al. | |

FOREIGN PATENT DOCUMENTS

| | | | |
|---|---|---|---|
| CA | 1076289 A | | 4/1980 |
| CN | 85105521 | * | 2/1986 |
| CN | 101189289 A | | 5/2008 |
| EP | 1122268 A1 | | 8/2001 |
| GB | 1399680 | * | 7/1972 |
| JP | 52-70000 A | | 6/1977 |
| JP | 09-059599 A | | 3/1997 |
| JP | 2004-277435 A | | 10/2004 |
| JP | 2004-277624 A | | 10/2004 |
| JP | 2007-217650 A | | 8/2007 |
| JP | 2009-067921 A | | 4/2009 |
| JP | 2010-138273 A | | 6/2010 |
| JP | 2011-021093 A | | 2/2011 |
| WO | 9902577 A1 | | 1/1999 |
| WO | 2012/014807 A1 | | 2/2012 |

OTHER PUBLICATIONS

English Translation of CN85105521, Feb. 7, 1986, pp. 1-4.*
International Search Report for PCT/JP2011/080405, Mailing Date of Apr. 17, 2012.
Office Action dated Apr. 8, 2014, issued in Chinese Patent Application No. 201180064382.9 with Partial English Translation (8 pages).
Extended European Search Report dated Nov. 10, 2014, issued in corresponding EP application No. 11855299.1 (6 pages).

* cited by examiner

*Primary Examiner* — Paul A Zucker
*Assistant Examiner* — Mark Luderer
(74) *Attorney, Agent, or Firm* — Westerman, Hattori, Daniels & Adrian, LLP

(57) ABSTRACT

A liquid resol-type phenolic resin obtained by reacting a phenol (A), and a secondary and/or tertiary alkylamine compound (B) in the presence of a basic catalyst. The nitrogen content relative to the total weight of the liquid resol-type phenolic resin is preferably from 3 to 30% by weight. Further, the secondary and/or tertiary alkylamine compound (B) is preferably hexamethylenetetramine. Moreover, the molar ratio between the phenol (A) and the secondary and/or tertiary alkylamine compound (B) preferably satisfies (B)/(A)=0.13 to 0.35.

5 Claims, No Drawings

US 9,657,139 B2

LIQUID RESOL-TYPE PHENOLIC RESIN

CROSS-REFERENCE TO RELATED APPLICATIONS

This application is a Continuation of copending application Ser. No. 13/979,063, filed on Jul. 10, 2013, which is a §371 National Stage Application of PCT International Application No. PCT/JP2011/080405 filed on Dec. 28, 2011, which claims a foreign priority of Japanese Patent Application No. 2011-005440 filed on Jan. 14, 2011. The entire contents of each of the above documents are hereby incorporated by reference into the present application.

TECHNICAL FIELD

The present invention relates to a liquid resol-type phenolic resin.

Priority is claimed on Japanese Patent Application No. 2011-005440, filed Jan. 14, 2011, the content of which is incorporated herein by reference.

BACKGROUND ART

Phenolic resins, which are thermosetting resins, are widely used as binders for bonding together materials that function as substrates, and because phenolic resins have excellent mechanical properties, electrical properties and adhesiveness, they are used in a wide variety of fields.

In order to obtain a molded item, a liquid phenolic resin is typically used by impregnating a substrate containing a fiber as a main component. Examples of this type of application include FRP, copper clad laminates, and wet paper friction materials.

Among such applications, the amount of friction materials using a phenolic resin as a binder is increasing in automobiles and railway carriages and the like. In particular, liquid resol-type phenolic resins are generally used for the friction materials used in the automatic transmission and the like of automatic vehicles, so-called wet friction materials. The properties demanded of these phenolic resins used in wet friction materials continue to increase year by year, and in particular, demands for increased flexibility of the phenolic resin have continued to grow, with the object of improving the coefficient of friction and the durability. However, despite having excellent mechanical properties, the cured products of typical phenolic resins tend to be hard and brittle, and cannot be said to exhibit excellent flexibility.

As a method of addressing the problems outlined above, tests are being conducted into improving the flexibility by using a drying oil or the like as a denaturant in the reaction used when synthesizing the phenolic resin (for example, see Patent Document 1).

However, this type of modified phenolic resin suffers a number of problems, including a marked deterioration in the strength after a heat history, and a short cycle life.

DOCUMENTS OF RELATED ART

Patent Document

[Patent Document 1] Japanese Unexamined Patent Application, First Publication No. Hei 9-59599

DISCLOSURE OF INVENTION

Problems to be Solved by the Invention

The present invention provides a liquid resol-type phenolic resin that can be used to obtain a molded item having the excellent properties of a phenolic resin, such as superior heat resistance and curability, as well as excellent flexibility.

Means to Solve the Problems

This type of object is achieved by the following aspects [1] to [5] of the present invention.

[1] A liquid resol-type phenolic resin obtained by reacting a phenol (A), and a secondary and/or tertiary alkylamine compound (B) in the presence of a basic catalyst.

[2] The liquid resol-type phenolic resin disclosed above in [1], wherein the nitrogen content relative to the total weight of the liquid resol-type phenolic resin is from 3 to 30% by weight.

[3] The liquid resol-type phenolic resin disclosed above in [1] of [2], wherein the secondary and/or tertiary alkylamine compound (B) is hexamethylenetetramine.

[4] The liquid resol-type phenolic resin disclosed above in any one of [1] to [3], wherein the phenol (A) and the secondary and/or tertiary alkylamine compound (B) are reacted in a molar ratio that satisfies (B)/(A)=0.13 to 0.35.

[5] The liquid resol-type phenolic resin disclosed above in any one of [1] to [4], which is used for impregnation.

Effects of the Invention

When the liquid resol-type phenolic resin of the present invention is used as a binder, a molded item having excellent heat resistance, curability and flexibility can be obtained.

MODES FOR CARRYING OUT THE INVENTION

A more detailed description of the liquid resol-type phenolic resin of the present invention is presented below, but the invention is in no way limited by these examples.

Additions, omissions, substitutions, and other modifications can be made without departing from the spirit or scope of the present invention.

The liquid resol-type phenolic resin of the present invention is obtained by reacting a phenol (A), and a secondary and/or tertiary alkylamine compound (B) in the presence of a basic catalyst.

Various methods can be used to obtain the liquid resol-type phenolic resin used in the present invention, and although there are no particular limitations on the method used, the liquid resol-type phenolic resin can be synthesized, for example, by reacting a typical phenol and a hexamine in the presence of a basic catalyst.

(A) Phenol

Examples of the phenol used in the liquid resol-type phenolic resin of the present invention include phenol, cresols such as o-cresol, m-cresol and p-cresol, xylenols such as 2,3-xylenol, 2,4-xylenol, 2,5-xylenol, 2,6-xylenol, 3,4-xylenol and 3,5-xylenol, ethylphenols such as o-ethylphenol, m-ethylphenol and p-ethylphenol, isopropylphenol, butylphenols such as butylphenol and p-tert-butylphenol, alkylphenols such as p-tert-amylphenol, p-octylphenol, p-nonylphenol and p-cumylphenol, halogenated phenols such as fluorophenol, chlorophenol, bromophenol and iodophenol, monohydric phenol substituted compounds such as p-phenylphenol, aminophenol, nitrophenol, dinitrophenol and trinitrophenol, as well as monohydric phenols such as 1-naphthol and 2-naphthol, and polyhydric phenols such as resorcinol, alkylresorcinols, pyrogallol, catechol, alkylcatechols, hydroquinone, alkylhydroquinones, phloroglucinol, bisphenol A, bisphenol F, bisphenol S and dihydroxynaphthalene. These compounds may be used individually, or two or more compounds may be used as a mixture. The phenol used in the present invention is preferably soluble in the organic solvent described below.

Among these phenols, a compound selected from among phenol, the cresols and bisphenol A is preferable. This enables an improvement in the mechanical strength of a molded item obtained using the liquid resol-type phenolic resin of the present invention.

(B) Secondary and/or Tertiary Alkylamine Compound

Examples of the secondary and/or tertiary alkylamine compound (B) used in the liquid resol-type phenolic resin of the present invention include secondary alkylamine compounds such as dimethylamine and diethylamine, and tertiary alkylamines compounds such as triethylamine, tetramethylethylenediamine and hexamethylenetetramine. These compounds may be used individually, or two or more compounds may be combined.

Among these compounds, the use of hexamethylenetetramine is preferable. By using hexamethylenetetramine, the reaction can be conducted without using an aldehyde source such as formalin.

Examples of the basic catalyst used in preparing the liquid resol-type phenolic resin of the present invention include alkali metal hydroxides such as sodium hydroxide, lithium hydroxide and potassium hydroxide, ammonia water, tertiary amines such as triethylamine, oxides and hydroxides of alkaline earth metals such as calcium, magnesium and barium, and other alkaline substances such as sodium carbonate. These compounds may be used individually, or two or more compounds may be combined. There are no particular limitations on the amount used of the basic catalyst, but the amount is typically within a range from 0.01 to 0.1 mol per 1 mol of the aforementioned phenol (A).

The proportions of the various components of the liquid resol-type phenolic resin of the present invention, relative to 1,000 parts by weight of the liquid resol-type phenolic resin, are from 0 to 100 parts by weight, and preferably from 0 to 50 parts by weight, of the phenol, from 0 to 80 parts by weight, and preferably from 0 to 40 parts by weight, of the secondary and/or tertiary alkylamine compound, and from 0 to 20 parts by weight, and preferably from 0 to 10 parts by weight, of the basic catalyst.

In the liquid resol-type phenolic resin of the present invention, the nitrogen content relative to the total weight of the liquid resol-type phenolic resin is preferably from 3 to 30% by weight. This nitrogen content is more preferably from 5 to 10% by weight.

If the nitrogen content is higher than this range, then the viscosity increases and it becomes difficult to take out the liquid resol-type phenolic resin from a vessel. Further, if the nitrogen content is less than this range, then the effect of the invention in improving the flexibility and the heat resistance diminishes.

In the liquid resol-type phenolic resin of the present invention, for each 1 mol of the phenol (A), the number of moles of the secondary and/or tertiary alkylamine compound (B) is preferably from 0.13 to 0.35 mol. This amount is more preferably from 0.18 to 0.30 mol.

This ensures that when the liquid resol-type phenolic resin of the present invention is used for impregnation, the resin exhibits good impregnation properties, and can also improve the flexibility of the molded item.

The liquid resol-type phenolic resin of the present invention is obtained by reacting the phenol (A) and the secondary and/or tertiary alkylamine compound (B) described above in the presence of the aforementioned basic catalyst. The reaction temperature is preferably from 50 to 110° C., and more preferably from 80 to 100° C.

In the liquid resol-type phenolic resin of the present invention, an organic solvent can be used to dilute the resin. There are no particular limitations on the organic solvent used for this dilution, and examples include alcohol-based organic solvents such as methanol, ethanol, isopropanol and butanol, ketone-based organic solvents such as acetone, methyl ethyl ketone and methyl isobutyl ketone, aromatic hydrocarbon solvents such as toluene and ethylbenzene, and mixtures of these solvents.

The liquid resol-type phenolic resin of the present invention can be used for impregnation. Impregnation refers to permeation of the resin into gaps within the texture or the structure of a substrate or the like. Examples of the substrate subjected to the impregnation include substrates formed using metal fiber, glass fiber, carbon fiber or chemical fiber or the like. The present invention can be used particularly favorably for wet paper friction material applications, and when used for a wet paper friction material application, a paper substrate containing not only the types of fiber components mentioned above, but also filled with a friction modifier such as cashew dust or diatomaceous earth or the like can be used.

The obtained molded item has the excellent properties of a phenolic resin such as superior heat resistance and curability, and also exhibits excellent flexibility.

EXAMPLES

The present invention is described below in further detail using a series of examples.

In the examples described below, "parts" refers to "parts by weight", and "%" refers to "% by weight".

Example 1

1. Production of Liquid Resol-Type Phenolic Resins

A reaction apparatus fitted with a stirrer, a reflux condenser and a thermometer was charged with 1,000 parts by weight of phenol, 370 parts by weight of hexamethylenetetramine (0.25 mol per 1 mol of phenol), 100 parts by weight of methanol, 100 parts by weight of acetone and 20 parts by weight of a 50% aqueous solution of sodium hydroxide, and the resulting mixture was heated to 95° C. and held at that temperature for 3 hours.

Subsequently, 1,200 parts by weight of acetone was added, and the temperature was cooled to 40° C. or lower, yielding 2,700 parts by weight of a liquid resol-type phenolic resin.

Example 2

With the exception of altering the amount of hexamethylenetetramine to 450 parts by weight (0.30 mol per 1 mol of phenol), preparation was performed using the same method as Example 1, yielding 2,780 parts by weight of a liquid resol-type phenolic resin.

Example 3

With the exception of altering the amount of hexamethylenetetramine to 270 parts by weight (0.18 mol per 1 mol of phenol), preparation was performed using the same method as Example 1, yielding 2,600 parts by weight of a liquid resol-type phenolic resin.

Example 4

With the exceptions of replacing the phenol from Example 1 with a mixed cresol containing 63% of meta-cresol and 27% of para-cresol, and altering the amount of hexamethylenetetramine to 320 parts by weight (0.25 mol per 1 mol of the phenol), preparation was performed using the same method as Example 1, yielding 2,650 parts by weight of a liquid resol-type phenolic resin.

Comparative Example 1

In Example 1, the 370 parts by weight of hexamethylenetetramine was replaced with 1,600 parts by weight of a 37% aqueous solution of formalin, and the reaction was conducted. The resultant was dewatered under reduced pressure at 80° C. for 30 minutes, 1,800 parts by weight of acetone was added, and the temperature was cooled to 40° C. or lower, yielding 4,100 parts by weight of a liquid resol-type phenolic resin.

2. Evaluation of Liquid Resol-Type Phenolic Resins

Using the liquid resol-type phenolic resins obtained in the examples and the comparative example, impregnated papers were prepared. Commercially available filter paper (120 mm×10 mm×thickness 1 mm) was used as the substrate.

The liquid resol-type phenolic resins obtained in the examples and the comparative example were each diluted with acetone to prepare a solution having a resin concentration of 30%, a sample of the aforementioned filter paper was impregnated with the solution, and the impregnated filter paper was then dried and cured in an oven at 190° C. for 30 minutes to obtain a test piece. The tensile strength of the thus obtained test piece was measured in accordance with JIS P 8113 "Paper and Board—Determination of Tensile Properties", under normal conditions and following treatment at 240° C. for 1 hour. Further, the Rockwell hardness of each test piece was measured in accordance with JIS K 7202 "Method of Rockwell Hardness Test for Plastics". The tensile strength was measured as an indicator of the mechanical strength of the cured product (molded item), and in the present invention, a higher numerical value is preferable. Further, the Rockwell hardness was measured as an indicator of the hardness of the cured product (molded item), and in the present invention, a lower numerical value is preferable.

The results of the above evaluations are summarized in Table 1.

Examples 1 to 4 are liquid resol-type phenolic resins of the present invention. It was found that the cured products of the obtained resins had superior flexibility as indicated by a low Rockwell hardness, and excellent heat resistance as indicated by a high degree of strength retention (tensile strength) following the heat treatment at 240° C.

In contrast, Comparative Example 1 is a resol-type resin obtained using phenol and formaldehyde, and the flexibility was poor as indicated by a high Rockwell hardness, and the reduction in the tensile strength following the heat treatment at 240° C. was large, indicating that a resin having excellent heat resistance could not be obtained.

INDUSTRIAL APPLICABILITY

The present invention can provide a liquid resol-type phenolic resin that can be used to obtain a molded item having the excellent properties of a phenolic resin, such as superior heat resistance and curability, as well as excellent flexibility. Accordingly, the present invention is extremely useful industrially.

The invention claimed is:

1. A method for producing a liquid resol-type phenolic resin, wherein the method comprises:
   mixing a phenol (A), a secondary and/or tertiary alkylamine compound (B) and a basic catalyst, and reacting the phenol (A), and the secondary and/or tertiary alkylamine compound (B) in presence of the basic catalyst,
   wherein the method does not use an aldehyde as a starting material,
   wherein the tertiary alkylamine compound is at least one selected from the group consisting of triethylamine, tetramethylethylenediamine and hexamethylenetetramine, and
   wherein a reaction temperature is from 50 to 110° C.,
   wherein the phenol (A) and the secondary and/or tertiary alkylamine compound (B) are reacted in a molar ratio that satisfies (B)/(A)=0.13 to 0.35.

2. A method for producing a liquid resol-type phenolic resin, comprising:
   mixing a phenol (A), a secondary and/or tertiary alkylamine compound (B) and a basic catalyst, and reacting the phenol (A), and the secondary and/or tertiary alkylamine compound (B) in presence of the basic catalyst,
   wherein the method does not use an aldehyde as a starting material,
   wherein a reaction temperature is from 50 to 110° C., and
   wherein the amount of atomic nitrogen relative to a total weight of the liquid resol-type phenolic resin is from 3 to 30% by weight.

3. The method according to claim 1, wherein the secondary and/or tertiary alkylamine compound (B) is hexamethylenetetramine.

TABLE 1

|  | Example 1 | Example 2 | Example 3 | Example 4 | Comparative Example 1 |
|---|---|---|---|---|---|
| Tensile strength under normal conditions (MPa) | 13.1 | 13.9 | 14.0 | 13.0 | 12.3 |
| Tensile strength following heat treatment at 240° C. (MPa) | 8.9 | 8.7 | 8.5 | 8.4 | 8.1 |
| Rockwell hardness | 75.5 | 74.0 | 74.0 | 76.0 | 83.3 |

4. A method for producing a liquid resol-type phenolic resin-impregnated substrate, comprising
applying the liquid resol-type phenolic resin defined in claim 1 to a substrate,
wherein the substrate is selected from the list consisting of metal fiber, glass fiber, and carbon fiber.

5. A method for producing a liquid resol-type phenolic resin, wherein the method comprises:
mixing a phenol (A), a secondary and/or tertiary alkylamine compound (B) and a basic catalyst, and reacting the phenol (A), and the secondary and/or tertiary alkylamine compound (B) in presence of the basic catalyst,
wherein the method does not use an aldehyde as a starting material,
wherein the tertiary alkylamine compound is at least one selected from the group consisting of triethylamine, tetramethylethylenediamine and hexamethylenetetramine, and
wherein a reaction temperature is from 50 to 110° C.,
wherein the secondary alkylamine compound is at least one selected from the group consisting of dimethylamine and diethylamine.

* * * * *